(12) United States Patent
Tsubuki et al.

(10) Patent No.: US 7,795,472 B2
(45) Date of Patent: Sep. 14, 2010

(54) PROCESS FOR PRODUCING 2-AMINO-2-[2-[4-(3-BENZYLOXY PHENYLTHIO)-2-CHLOROPHENYL] ETHYL]-1,3-PROPANEDIOL HYDROCHLORIDE AND HYDRATES THEREOF, AND INTERMEDIATES IN THE PRODUCTION THEREOF

(75) Inventors: Takeshi Tsubuki, Oyama (JP); Kenichi Kobayashi, Koshigaya (JP); Hidetaka Komatsu, Shimotsuga-gun (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 276 days.

(21) Appl. No.: 11/665,058

(22) PCT Filed: Oct. 7, 2005

(86) PCT No.: PCT/JP2005/018602

§ 371 (c)(1),
(2), (4) Date: May 15, 2007

(87) PCT Pub. No.: WO2006/041019

PCT Pub. Date: Apr. 20, 2006

(65) Prior Publication Data

US 2008/0207941 A1    Aug. 28, 2008

(30) Foreign Application Priority Data

Oct. 12, 2004    (JP) .............................. 2004-297651

(51) Int. Cl.
C07C 215/00    (2006.01)
C07C 321/00    (2006.01)
C07C 323/00    (2006.01)
C07C 381/00    (2006.01)
C07C 209/00    (2006.01)
C07C 213/00    (2006.01)

(52) U.S. Cl. ....................... 564/355; 564/341; 564/415; 564/416; 564/417; 564/418; 564/420; 564/423

(58) Field of Classification Search ........................ None
See application file for complete search history.

(56) References Cited

U.S. PATENT DOCUMENTS

| | | | |
|---|---|---|---|
| 5,447,922 A | 9/1995 | Lawrence et al. | |
| 5,475,138 A * | 12/1995 | Pal et al. ..................... | 564/355 |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,960,692 B2 | 11/2005 | Kohno et al. | |
| 6,963,012 B2 | 11/2005 | Kohno et al. | |
| 7,456,157 B2 | 11/2008 | Kohno et al. | |
| 7,482,491 B2 * | 1/2009 | Kohno et al. ................. | 564/355 |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147490 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |

(Continued)

FOREIGN PATENT DOCUMENTS

JP        2002-53575        2/2002

(Continued)

OTHER PUBLICATIONS

Barua et al. Synlett 2001, No. 9, 1411-1444.*

(Continued)

*Primary Examiner*—Daniel M Sullivan
*Assistant Examiner*—Clinton Brooks
(74) *Attorney, Agent, or Firm*—Wenderoth, Lind & Ponack, L.L.P.

(57) ABSTRACT

A process for the industrial production of 2-amino-2-[2-[4-(3-benzyloxyphenylthio)-2-chlorophenyl]ethyl]-1,3-propanediol hydrochloride (Compound I), an effective immunosuppressant.

The process for producing 2-amino-2-[2-[4-(3-benzyloxyphenylthio)-2-chlorophenyl]ethyl]-1,3-propanediol hydrochloride or a hydrate thereof includes the steps of reacting 4-(3-benzyloxyphenylthio)-2-chlorobenzaldehyde with ethyl diethylphosphonoacetate in a solvent in the presence of a base to form ethyl 3-[4-(3-benzyloxyphenylthio)-2-chlorophenyl]acrylate; reducing the resulting ethyl 3-[4-(3-benzyloxyphenylthio)-2-chlorophenyl]acrylate, followed by mesylation, iodination and nitration, to form 1-benzyloxy-3-[3-chloro-4-(3-nitropropyl)phenylthio]benzene; forming 2-[2-[4-(3-benzyloxyphenylthio)-2-chlorophenyl]ethyl]-2-nitro-1,3-propanediol using a formaldehyde solution; and reducing the resulting 2-[2-[4-(3-benzyloxyphenylthio)-2-chlorophenyl]ethyl]-2-nitro-1,3-propanediol to form the desired product.

4 Claims, No Drawings

U.S. PATENT DOCUMENTS

| | | |
|---|---|---|
| 2005/0222422 A1 | 10/2005 | Lynch et al. |
| 2005/0245575 A1 | 11/2005 | Chen et al. |
| 2006/0046979 A1 | 3/2006 | Foster et al. |
| 2006/0089334 A1 | 4/2006 | Budhu et al. |
| 2006/0135622 A1 | 6/2006 | Kohno et al. |
| 2006/0135786 A1 | 6/2006 | Saha et al. |
| 2006/0148830 A1 | 7/2006 | Terakado et al. |
| 2006/0148844 A1 | 7/2006 | Nakade et al. |
| 2006/0160771 A1 | 7/2006 | Kohno et al. |
| 2006/0161005 A1 | 7/2006 | Doherty et al. |
| 2006/0166940 A1 | 7/2006 | Buehlmayer et al. |
| 2006/0211656 A1 | 9/2006 | Albert et al. |
| 2006/0211658 A1 | 9/2006 | Hinterding et al. |
| 2006/0252741 A1 | 11/2006 | Colandrea et al. |
| 2006/0264403 A1 | 11/2006 | Albert |
| 2007/0010494 A1 | 1/2007 | Ehrhardt et al. |
| 2007/0043014 A1 | 2/2007 | Doherty et al. |
| 2007/0088002 A1 | 4/2007 | Lynch et al. |
| 2007/0135501 A1 | 6/2007 | Hinterding et al. |
| 2007/0149597 A1 | 6/2007 | Nishi et al. |
| 2007/0167410 A1 | 7/2007 | Pan et al. |
| 2007/0167425 A1 | 7/2007 | Nakade et al. |
| 2007/0191468 A1 | 8/2007 | Nishi et al. |
| 2007/0203100 A1 | 8/2007 | Pan et al. |
| 2007/0225260 A1 | 9/2007 | Hinterding et al. |
| 2008/0025973 A1 | 1/2008 | Fleenor et al. |
| 2008/0027508 A1 | 1/2008 | Chu |
| 2008/0032923 A1 | 2/2008 | Kudou et al. |
| 2008/0153882 A1 | 6/2008 | Nishi et al. |
| 2008/0161410 A1 | 7/2008 | Kusters et al. |
| 2008/0200438 A1 | 8/2008 | Albert et al. |
| 2008/0207584 A1 | 8/2008 | Habashita et al. |
| 2008/0207941 A1 | 8/2008 | Tsubuki et al. |
| 2008/0249093 A1 | 10/2008 | Colandrea et al. |
| 2009/0023797 A1 | 1/2009 | Azzaoui et al. |

FOREIGN PATENT DOCUMENTS

| | | |
|---|---|---|
| JP | 2002-316985 | 10/2002 |
| JP | 2003-137894 | 5/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-47899 | 2/2005 |
| JP | 2005-247691 | 9/2005 |
| WO | 01/98301 | 12/2001 |
| WO | 03/029205 | 4/2003 |
| WO | 2004/026817 | 4/2004 |
| WO | 2004/074297 | 9/2004 |
| WO | 2005/014525 | 2/2005 |
| WO | 2005/014603 | 2/2005 |
| WO | 2005/063671 | 7/2005 |
| WO | 2006/041015 | 4/2006 |
| WO | 2006/063033 | 6/2006 |
| WO | 2006/129688 | 12/2006 |
| WO | 2007/043433 | 4/2007 |
| WO | 2007/043568 | 4/2007 |
| WO | 2007/091501 | 8/2007 |

OTHER PUBLICATIONS

Kornblum, N. et al. J. Am. Chem. Soc., 1956, 78(7), 1497-1501.*
Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.
Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.
Yasuyuki Igarashi, Sphingosine-1-Phosphate as an Intercellular Signaling Molecule, Ann. NY Acad. Sci., 1998, vol. 845, pp. 19-31.
Jacobs et al., Intramuscular Interferon Beta-1a for Disease Progression in Relapsing Multiple Sclerosis, Ann. Neurol., 1996, vol. 39, No. 3, pp. 285-294.
Weinshenker et al., A Randomized Trial of Plasma Exchange in Acute Central Nervous System Inflammatory Demyelinating Disease, Ann. Neurol., 1999, vol. 46, No. 6, pp. 878-886.
Ganem et al., The Molecular Biology of the Hepatitis B Virus, Annu. Rev. Biochem., 1987, vol. 56 pp. 651-693.
Kaneko et al., Sphingosine-1-phosphate receptor agonists suppress concanavalin A-induced hepatic injury in mice, Biochem. and Biophys. Res. Commun., 2006, vol. 345, pp. 85-92.
Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.
Klein et al., Total Synthesis and Antifungal Evaluation of Cyclic Aminohexapeptides, Bioorg. Med. Chem., 2000, vol. 8, pp. 167-1696.
Hashimoto et al., β-Phenylselenoalanine as a dehydroalanine precursor-efficient synthesis of alternariolide (Am-toxin I), Chem. Commun., 1996, pp. 1139-1140.
Levkau et al., High-Density Lipoprotein Stimulates Myocardial Perfusion in Vivo, Circulation, 2004, vol. 110, pp. 3355-3359.
Salomone et al., S1P$_3$ receptors mediate the potent constriction of cerebral arteries by sphingosine-1-phosphate, Eur. J. Pharmacol., 2003, vol. 469, pp. 125-134.
Heneghan et al., Current and Novel Immunosuppressive Therapy for Autoimmune Hepatitis, Hepatology, 2002, vol. 35, No. 1, pp. 7-13.
Francis V. Chisari, Cytotoxic T Cells and Viral Hepatitis, J. Clin. Invest., Apr. 1997, vol. 99, No. 7, pp. 1472-1477.
Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.
Brinkmann et al., The Immune Modulator FTY720 Targets Sphingosine 1-Phosphate Receptors, J. Biol. Chem., 2002, vol. 277, No. 24, pp. 21453-21457.
Sanna et al., Sphingosine 1-Phosphate (S1P) Receptor Subtypes S1P$_1$ and S1P$_3$, Respectively, Regulate Lymphocyte Recirculation and Heart Rate, J. Biol. Chem., Apr. 2, 2004, vol. 279, No. 14, pp. 13839-13848.
Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.
George C. Ebers, Randomised double-blind placebo-controlled study of interferon β-1a in relapsing/remitting multiple sclerosis, Lancet, Nov. 7, 1998, vol. 352, pp. 1498-1501.
Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.
Fried et al., Peginterferon Alfa-2a Plus Ribavirin for Chronic Hepatitis C Virus Infection, N. Engl. J. Med., Sep. 26, 2002, vol. 347, No. 13, pp. 975-982.
Mailliard et al., Suppressing Hepatitis B without Resistance—So Far, So Good, N. Engl. J. Med., Feb. 27, 2003, vol. 348, No. 9, pp. 848-850.
Niessen et al., Dentritic cell PAR1-S1P3 signalling couples coagulation and inflammation, Nature, Apr. 3, 2008, vol. 452, No. 3, pp. 654-658.
IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.
Paty et al., Interferon beta-1b is effective in relapsing-remitting multiple sclerosis. II. MRI analysis results of a multicenter, randomized, double-blind, placebo-controlled trial, Neurology, Apr. 1993, vol. 43, pp. 662-667.

Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.

Zivadinov et al., Effects of IV methylprednisolone on brain atrophy in relapsing-remitting MS, Neurology, 2001, vol. 57, pp. 1239-1247.

Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.

Rudick et al., Management of Multiple Cclerosis, N. Engl. J. Med., Nov. 27, 1997, vol. 337, No. 22, pp. 1604-1611.

Daniel K. Podolsky, Inflammatory Bowel Disease, N. Engl. J. Med., Aug. 8, 2002, vol. 347, No. 6, pp. 417-429.

Kappos et al., Oral Fingolimod (FTY720) for Relapsing Multiple Sclerosis, N. Engl. J. Med., Sep. 14, 2006, vol. 355, No. 11, pp. 1124-1140.

Viscido et al., Inflammatory bowel diseases: clinical update of practical guidelines, Nucl. Med. Commun., 2005, vol. 26, No. 7, pp. 649-655.

Gon et al., $S1P_3$ receptor-induced reorganization of epithelial tight junctions comprises lung barrier integrity and is potentiated by TNF, PNAS, Jun. 28, 2005, vol. 102, No. 26, pp. 9270-9275.

Saito et al., Hepatitis C virus infection is associated with the development of hepatocellular carcinoma, Proc. Natl. Acad. Sci. USA, Sep. 1990, vol. 87, pp. 6547-6549.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrahedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

* cited by examiner

PROCESS FOR PRODUCING 2-AMINO-2-[2-[4-(3-BENZYLOXY PHENYLTHIO)-2-CHLOROPHENYL] ETHYL]-1,3-PROPANEDIOL HYDROCHLORIDE AND HYDRATES THEREOF, AND INTERMEDIATES IN THE PRODUCTION THEREOF

TECHNICAL FIELD

The present invention relates to a process for producing 2-amino-2-[2-[4-(3-benzyloxyphenylthio)-2-chlorophenyl]ethyl]-1,3-propanediol hydrochloride (which may be referred to simply as "Compound I," hereinafter), an effective immunosuppressant that has little side effects. The present invention also relates to novel intermediates in the production of Compound I.

BACKGROUND ART

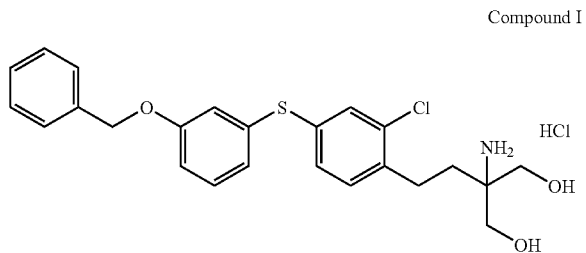

Compound I

Compound I is a derivative of 2-amino-1,3-propanediol that has a substituted diarylsulfide structure and acts as a potent immunosuppressant. It is a pharmaceutically useful compound effective in the treatment of various diseases (including autoimmune diseases such as a rheumatoid arthritis, nephritis, gonarthrosis and systemic lupus erythematosus, chronic inflammatory diseases such as inflammatory bowel disease, and allergic diseases such as asthma and dermatitis) (The compound is described in Example 46 in Patent Document 1). Even a production process of Compound I is specifically described in the International Publication Pamphlet of Patent Document 1. The process, however, is difficult to implement on an industrial scale and requires further improvements in many aspects, including operation, purification efficiency and yields of the product. There thus is a significant need for a practical process for the industrial production of Compound I.

Patent Document 1 WO03/029205 pamphlet

DISCLOSURE OF THE INVENTION

Problems to be Solved by the Invention

Requirements for the industrial production of Compound I as a high quality pharmaceutical product include development of novel practical intermediates, elimination of the purification step by column chromatography, improvements in the operation of the process and the yields and purity of the product, and reduction in the use of harmful solvents.

Means for Solving the Problems

In the course of studies to find a way to meet these requirements, the present inventors have found that novel compounds ethyl 3-[4-(3-benzyloxyphenylthio)-2-chlorophenyl]acrylate, 1-benzyloxy-3-[3-chloro-4-(3-nitropropyl)phenylthio]benzene and 2-[2-[4-(3-benzyloxyphenylthio)-2-chlorophenyl]ethyl]-2-nitro-1,3-propanediol can be used as intermediates in the production of Compound I and the use of these intermediates enables simple and industrially practical production of Compound I. It is this discovery that ultimately led to the present invention.

Specifically, the present invention concerns the following:

1) A process for producing 2-amino-2-[2-[4-(3-benzyloxyphenylthio)-2-chlorophenyl]ethyl]-1,3-propanediol hydrochloride or a hydrate thereof, comprising the steps of:

reacting 4-(3-benzyloxyphenylthio)-2-chlorobenzaldehyde with ethyl diethylphosphonoacetate in a solvent in the presence of a base to form ethyl 3-[4-(3-benzyloxyphenylthio)-2-chlorophenyl]acrylate;

reducing the resulting ethyl 3-[4-(3-benzyloxyphenylthio)-2-chlorophenyl]acrylate, followed by mesylation, iodination and nitration, to form 1-benzyloxy-3-[3-chloro-4-(3-nitropropyl)phenylthio]benzene;

hydroxymethylating the resulting 1-benzyloxy-3-[3-chloro-4-(3-nitropropyl)phenylthio]benzene with formaldehyde to form 2-[2-[4-(3-benzyloxyphenylthio)-2-chlorophenyl]ethyl]-2-nitro-1,3-propanediol; and reducing the resulting 2-[2-[4-(3-benzyloxyphenylthio)-2-chlorophenyl]ethyl]-2-nitro-1,3-propanediol to form the desired product.

2) An intermediate in the production of 2-amino-2-[2-[4-(3-benzyloxyphenylthio)-2-chlorophenyl]ethyl]-1,3-propanediol hydrochloride or a hydrate thereof, comprising a novel compound ethyl 3-[4-(3-benzyloxyphenylthio)-2-chlorophenyl]acrylate or a hydrate thereof.

3) An intermediate in the production of 2-amino-2-[2-[4-(3-benzyloxyphenylthio)-2-chlorophenyl]ethyl]-1,3-propanediol hydrochloride or a hydrate thereof, comprising a novel compound 1-benzyloxy-3-[3-chloro-4-(3-nitropropyl)phenylthio]benzene or a hydrate thereof.

4) An intermediate in the production of 2-amino-2-[2-[4-(3-benzyloxyphenylthio)-2-chlorophenyl]ethyl]-1,3-propanediol hydrochloride or a hydrate thereof, comprising a novel compound 2-[2-[4-(3-benzyloxyphenylthio)-2-chlorophenyl]ethyl]-2-nitro-1,3-propanediol or a hydrate thereof.

ADVANTAGES OF THE INVENTION

Compounds of the present invention serving as raw materials, ethyl 3-[4-(3-benzyloxyphenylthio)-2-chlorophenyl]acrylate, 1-benzyloxy-3-[3-chloro-4-(3-nitropropyl)phenylthio]benzene and 2-[2-[4-(3-benzyloxyphenylthio)-2-chlorophenyl]ethyl]-2-nitro-1,3-propanediol and their hydrates, are novel compounds that have never been described, nor has their usefulness ever been discussed. Each of ethyl 3-[4-(3-benzyloxyphenylthio)-2-chlorophenyl]acrylate, 1-benzyloxy-3-[3-chloro-4-(3-nitropropyl)phenylthio]benzene and 2-[2-[4-(3-benzyloxyphenylthio)-2-chlorophenyl]ethyl]-2-nitro-1,3-propanediol can serve as an intermediate in the production of Compound I and each allows stable and high yield practical production of Compound I with simple purification method. Thus, the use of the compounds of the present invention for the first time enables industrially production of Compound I.

BEST MODE FOR CARRYING OUT THE PRESENT INVENTION

The process of the present invention, which enables industrial scale production of Compound I, is carried out as follows (See also Scheme I): Ethyl 3-[4-(3-benzyloxyphenylthio)-2-chlorophenyl]acrylate is reduced using bismuth trichloride and sodium borohydride. The reduced product is further reduced using potassium borohydride and lithium chloride. The resulting alcohol derivative is mesylated by reacting with methanesulfonyl chloride. The mesylated product is iodinated with sodium iodide and then reacted with sodium nitrite to form 1-benzyloxy-3-[3-chloro-4-(3-nitropropyl)phenylthio]benzene. This product is reacted with formaldehyde in the presence of a base to form 2-[2-[4-(3-benzyloxyphenylthio)-2-chlorophenyl]ethyl]-2-nitro-1,3-propanediol. Reducing this compound with palladium hydroxide-carbon gives Compound I.

We now describe a process for obtaining the novel compounds of the present invention serving as raw materials, i.e., ethyl 3-[4-(3-benzyloxyphenylthio)-2-chlorophenyl]acrylate (3), 1-benzyloxy-3-[3-chloro-4-(3-nitropropyl)phenylthio]benzene (8), and 2-[2-[4-(3-benzyloxyphenylthio)-2-chlorophenyl]ethyl]-2-nitro-1,3-propanediol (9), and hydrates thereof.

A mixture of 4-(3-benzyloxyphenylthio)-2-chlorobenzaldehyde (1) and ethyl diethylphosphonoacetate (2) is stirred for 3 to 8 hours at 50 to 80° C. in an organic solvent, such as dimethylformamide or dimethylsulfoxide, in the presence of a base, such as potassium bicarbonate, sodium bicarbonate, potassium carbonate or sodium carbonate. Subsequently, the

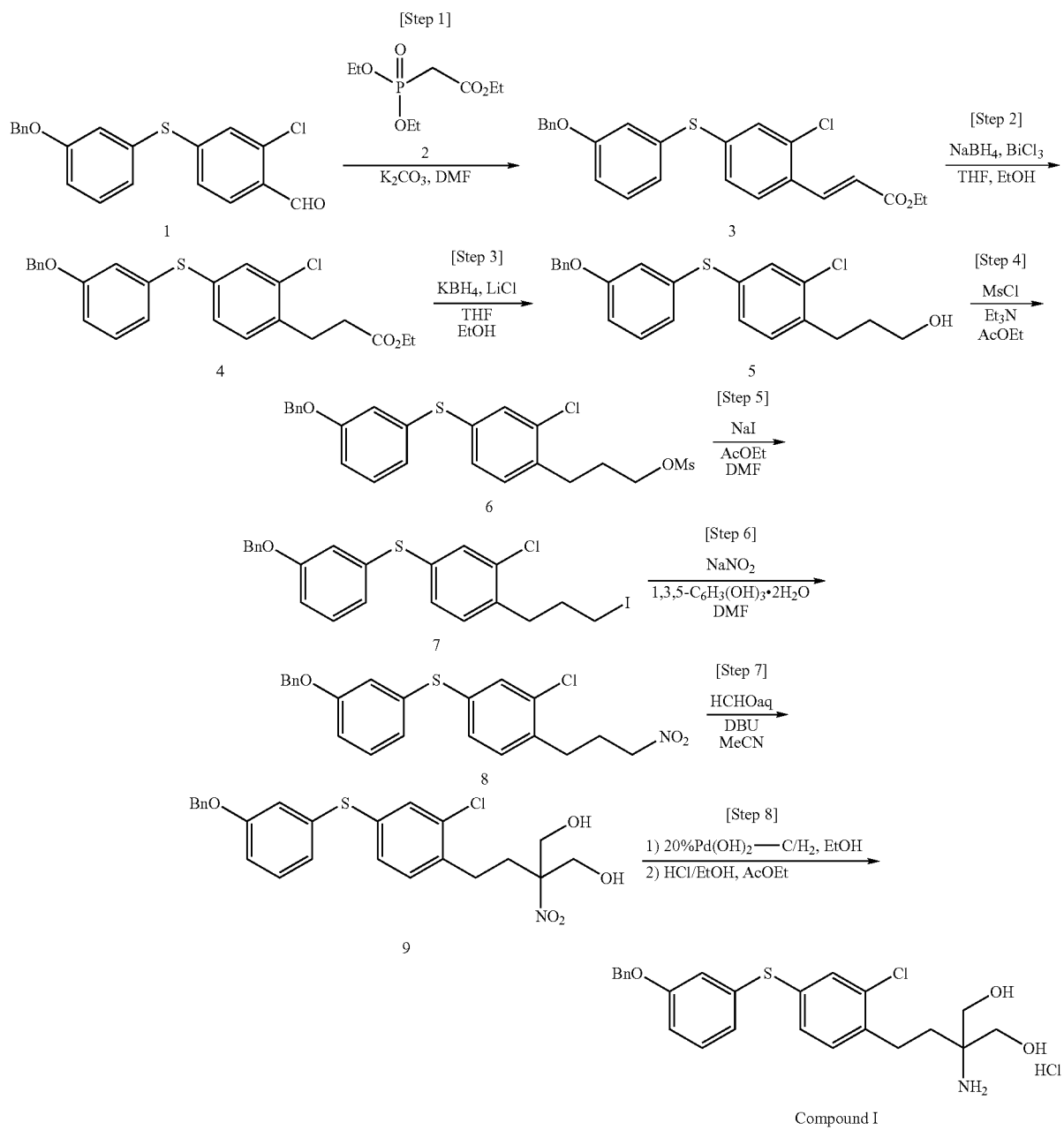

reaction mixture is chilled in an ice water bath while being stirred and water is added. The resulting crystals are collected by filtration and washed with aqueous 2-propanol to give ethyl 3-[4-(3-benzyloxyphenylthio)-2-chlorophenyl]acrylate (3) as crude crystals. This product is dissolved in ethylacetate and the mixture was washed with water. The organic layer is concentrated under reduced pressure to obtain a pale yellow oil. To this product, acetone is added and the mixture is stirred while being chilled to form crystals (Crystal seeds are added when necessary). Water is then added and the mixture is stirred while being chilled. The resulting crystals are collected by filtration and washed with acetone-water. The crystals are then dried at 40° C. or below to give ethyl 3-[4-(3-benzyloxyphenylthio)-2-chlorophenyl]acrylate (3) or a hydrate thereof.

Subsequently, ethyl 3-[4-(3-benzyloxyphenylthio)-2-chlorophenyl]acrylate (3) is dissolved in tetrahydrofuran or an alcohol, such as methanol and ethanol, or a mixture thereof. While the mixture is stirred at 30 to 40° C., bismuth trichloride and sodium borohydride are added. Additional bismuth trichloride and sodium borohydride are added to complete the reduction. The product is treated to give a pale yellow oil. This product is dissolved in an organic solvent such as tetrahydrofuran. While the mixture is kept at 25° C. or below, potassium borohydride, lithium chloride and an alcohol, such as methanol and ethanol, are added. The mixture is stirred at 30 to 50° C. for 1 to 3 hours and is then treated. The resulting faint yellow oil is dissolved in an organic solvent such as ethyl acetate. Methanesulfonyl chloride is then added at 20° C. or below in the presence of a base such as triethylamine and pyridine. The mixture is stirred for 1 to 3 hours and is then treated to obtain a pale yellow oil. This product is dissolved in a mixed solvent composed for example of ethyl acetate and dimethylformamide. Sodium iodide is then added while the mixture is being stirred and the resulting mixture is stirred at 50 to 80° C. for 3 to 5 hours. The product is treated to give a yellow oil. This oily product is dissolved in an organic solvent such as dimethylformamide, and phloroglucinol and sodium nitrite are added while the mixture is being stirred. Stirring is continued for additional 4 to 6 hours at 20 to 35° C. Subsequently, sodium thiosulfate pentahydrate in brine is added and the mixture is treated and purified to give 1-benzyloxy-3-[3-chloro-4-(3-nitropropyl)phenylthio]benzene (8) or a hydrate thereof as a pale yellow oil.

1-Benzyloxy-3-[3-chloro-4-(3-nitropropyl)phenylthio]benzene (8) is dissolved in an organic solvent, such as acetonitrile and tetrahydrofuran. While the mixture is chilled in an ice bath, a formaldehyde solution is added and the reaction is allowed to proceed at 0 to 60° C. for 1 to 3 hours in the presence of a base, such as 1,8-diazabicyclo[5.4.0]undeca-7-ene, 1,5-diazabicyclo[4.3.0]non-5-ene, diazabicyclo[2.2.2]octane, trialkylamine, sodium hydroxide and potassium hydroxide. Subsequently, the product is treated to give 2-[2-[4-(3-benzyloxyphenylthio)-2-chlorophenyl]ethyl]-2-nitro-1,3-propanediol (9) or a hydrate thereof.

2-[2-[4-(3-Benzyloxyphenylthio)-2-chlorophenyl]ethyl]-2-nitro-1,3-propanediol (9) is reduced in an organic solvent such as ethanol in the presence of a catalyst such as palladium hydroxide-carbon at room temperature to 60° C. under a hydrogen pressure of atmospheric pressure to 507 kPa. This gives 2-amino-2-[2-[4-(3-benzyloxyphenylthio)-2-chlorophenyl]ethyl]-1,3-propanediol. This product is dissolved in an organic solvent, such as ethanol, 2-propanol and ethyl acetate, or a mixture thereof and is reacted with hydrochloric acid. This gives 2-amino-2-[2-[4-(3-benzyloxyphenylthio)-2-chlorophenyl]ethyl]-1,3-propanediol hydrochloride (Compound I). The above-described process enables simple production of Compound I in high yield and purity.

The starting material 4-(3-benzyloxyphenylthio)-2-chlorobenzaldehyde (1) can readily be obtained by converting commercially available 3-benzyloxyphenol (10) into a thiophenol derivative by dimethylthiocarbamate method (J. Org. Chem., 31, 3980 (1966).) and reacting the thiophenol derivative with commercially available 2-chloro-4-fluorobenzaldehyde (See Scheme II).

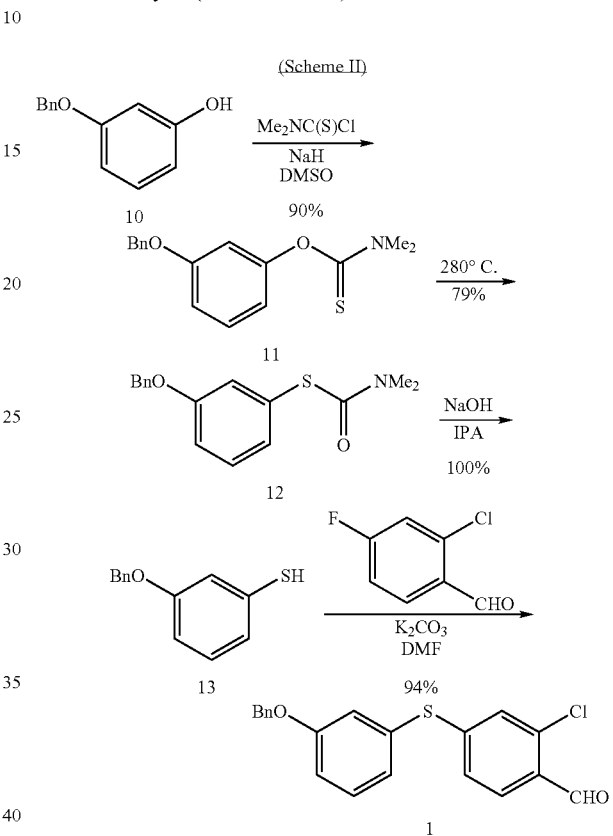

As described above, the present invention provides an effective process for the industrial production of Compound I.

EXAMPLES

The present invention will now be described with reference to specific examples, which are not intended to limit the scope of the invention in any way.

Reference Example 1

O-(3-Benzyloxy)phenyldimethylthiocarbamate (11)

A 60% sodium hydride (19.9 g, 498 mmol) was slowly added to a solution of 3-benzyloxyphenol (10) (83.0 g, 415 mmol) in dehydrated dimethylsulfoxide (DMSO) (415 mL) while the solution was water-cooled and stirred. The mixture was stirred for 30 min. Subsequently, dimethylthiocarbamoyl chloride (61.5 g, 498 mmol) was slowly added while the mixture was water-cooled and stirred. The mixture was then stirred at room temperature for 1.5 hours. Subsequently, the reaction mixture was slowly poured into ice water (2 L) and was extracted with ethyl acetate twice (1.5 L and 500 mL) The organic layers were combined, washed sequentially with water (2 L) and 28% brine (1 L) and then dried over anhydrous sodium sulfate. The solvent was evaporated and the residue was subjected to silica gel column chromatography (silica gel 60, 3 L, hexane:ethyl acetate=10:1->5:1) to give O-(3-benzyloxy)phenyldimethylthiocarbamate (2) as a pale yellow oil (107 g, 90%).

400 MHz $^1$H-NMR (CDCl$_3$) δ; 3.32 (3H, s), 3.45 (3H, s), 5.04 (2H, s), 6.68-6.73 (2H, m), 6.86-6.89 (1H, m), 7.25-7.44 (6H, m).

EI-MS m/z; 287 (M$^+$).

Reference Example 2

S-(3-Benzyloxy)phenyldimethylthiocarbamate (12)

O-(3-Benzyloxy)phenyldimethylthiocarbamate (11) (100 g, 348 mmol) was stirred for 1 hour at an internal temperature of 270 to 285° C. under reduced pressure (4.53 kPa). Subsequently, the mixture was allowed to cool at room temperature and diisopropyl ether (200 mL) was added at an internal temperature of 50° C. The mixture was stirred at room temperature for crystallization. Diisopropylether (100 mL) was then added and the mixture was stirred for 1 hour while being cooled in ice water. The resulting crystals were collected by filtration and washed with diisopropyl ether (50 mL) which had been cooled with ice. The washed product was then dried for 3 hours under reduced pressure to give S-(3-benzyloxy) phenyldimethylthiocarbamate (3) as white powdery crystals (79.3 g, 79%).

MP 68-69° C.

400 MHz $^1$H-NMR (CDCl$_3$) δ; 3.04 (3H, br s), 3.09 (3H, br s), 5.05 (2H, s), 6.99-7.16 (3H, m), 7.27-7.44 (6H, m).

EI-MS m/z; 287 (M$^+$).

Reference Example 3

3-Benzyloxybenzenethiol (13)

To S-(3-benzyloxy)phenyldimethylthiocarbamate (12) (40.0 g, 139 mmol), 2-propanol (160 mL), sodium hydroxide (22.2 g, 556 mmol) and purified water (80 mL) were added and the mixture was refluxed for 6 hours in an argon atmosphere. Subsequently, the mixture was stirred in ice water and 6 mol/L hydrochloric acid (120 mL) was added dropwise. Purified water (300 mL) was then added and the resulting crystals were collected by filtration. This product was washed with a 20% aqueous 2-propanol (300 mL) and the washed product was air-dried at room temperature for 2 days to give 3-benzyloxybenzenethiol (4) as a pale yellow powdery crystals (30.1 g, 100%).

MP 49-50° C.

400 MHz $^1$H-NMR (d$_6$-DMSO) δ; 5.06 (2H, s), 5.41 (1H, s), 6.74-6.97 (3H, m), 7.14 (1H, t, J=7.8 Hz), 7.30-7.44 (5H, m).

EI-MS m/z; 216 (M$^+$).

Reference Example 4

4-(3-Benzyloxyphenylthio)-2-chlorobenzaldehyde (1)

3-Benzyloxybenzenethiol (13) (75.0 g, 347 mmol) and 2-chloro-4-fluorobenzaldehyde (55.0 g, 347 mmol) were dissolved in dimethylformamide (DMF) (350 mL) while the solution was being stirred. The solution was then placed in a water bath at 30° C. and potassium carbonate (62.3 g, 451 mmol) and dimethylformamide (25 mL) were added. This mixture was stirred for 30 min at an internal temperature of 40 to 42° C. Tap water (125 mL) was added and the mixture was cooled in ice water. To the cooled mixture, additional tap water (625 mL) was added dropwise for crystallization. The mixture was stirred for 30 min and the resulting crystals were collected by filtration and washed with 10% aqueous 2-propanol (188 mL). The moist crystals were dissolved in ethyl acetate (750 mL) and the solution was washed twice with tap water (375 mL×2). The organic layer was concentrated under reduced pressure and acetone (900 mL) was added to the resulting residue. Purified water (386 mL) was then added dropwise at an internal temperature of 23° C. The mixture was stirred for 30 min and the resulting crystals were collected by filtration and washed with 50% aqueous acetone (400 mL). The washed crystals were air-dried overnight. Subsequently, the product was dried by blowing an air stream at 45° C. for 1 hour. This gave 4-(3-benzyloxyphenylthio)-2-chlorobenzaldehyde (1) as a colorless prism crystals (115 g, 94%).

MP 58-59° C.

400 MHz $^1$H-NMR (CDCl$_3$) δ; 5.07 (2H, s), 7.04-7.14 (5H, m), 7.31-7.43 (6H, m), 7.75 (1H, d, J=8.3 Hz), 10.35 (1H, d, J=0.7 Hz).

EI-MS m/z; 354 (M$^+$).

Example 1

Ethyl 3-[4-(3-benzyloxyphenylthio)-2-chlorophenyl] acrylate (3)

4-(3-Benzyloxyphenylthio)-2-chlorobenzaldehyde (1) (115 g) (325 mmol) and ethyl diethylphosphonoacetate (2) (94.6 g, 422 mmol) were added to dimethylformamide (DMF) (518 mL). The mixture was stirred to dissolve the compounds. Potassium carbonate (58.3 g, 422 mmol) was then added and the mixture was stirred at an internal temperature of 70 to 73° C. for 5.5 hours.

While the mixture was water-cooled and stirred at an internal temperature of 40° C., tap water (95 mL) was added and the mixture was further stirred while being chilled. At an internal temperature of 10° C., water (5 mL) and crystal seeds were added and the formation of crystals was confirmed. Subsequently, tap water (936 mL) was slowly added dropwise and the mixture was stirred for 30 min at an internal temperature of 3 to 10° C. The crystallized solid was collected by filtration and washed with 10% aqueous 2-propanol (518 mL) to obtain moist crystals as a crude product. This product was dissolved in ethyl acetate (806 mL) and the solution was washed twice with water (403 mL).

The organic layer was concentrated under reduced pressure and the concentrate was dried for 30 min at an external temperature of 50° C. under reduced pressure to give a pale yellow oil. This product was dissolved in acetone (691 mL). While the mixture was chilled and stirred, purified water (95 mL) and crystal seeds were added at an internal temperature of 5 to 10° C. for crystallization. The mixture was further stirred for 5 min while being chilled. Subsequently, purified water (366 mL) was added dropwise and the mixture was stirred for 30 min at an internal temperature of 5 to 10° C.

The crystallized solid was collected by filtration and was washed with 40% aqueous acetone (461 mL) (internal temperature=4° C.). The washed product was dried for 50 min under an air stream and was subsequently air-dried at room temperature. The product was further dried at 38° C. for 8 hours under an air stream. This gave Compound (3) as faint yellow granular crystals (136 g, 320 mmol, 98% yield).

mp 45-47° C. (hot plate method).

EI-MS m/z: 424 (M$^+$).

$^1$H-NMR (CDCl$_3$, 400 MHz) δ: 1.34 (3H, t, J=7.1 Hz), 4.27 (2H, q, J=7.1 Hz), 5.05 (2H, s), 6.38 (1H, d, J=16.1 Hz), 6.92-7.11 (4H, m), 7.23-7.49 (8H, m), 8.02 (1H, d, J=15.9 Hz).

Example 2

1-Benzyloxy-3-[3-chloro-4-(3-nitropropyl)phenylthio]benzene (8)

Tetrahydrofuran (THF) (405 mL) and ethanol (405 mL) were added to ethyl 3-[4-(3-benzyloxyphenylthio)-2-chlorophenyl]acrylate (3) (135 g, 318 mmol). While the mixture was stirred at an internal temperature of 35° C., bismuth trichloride (25.0 g, 79.4 mmol) was added, followed by slow addition of sodium borohydride (15.0 g, 397 mmol). The mixture was further stirred while being cooled and additional sodium borohydride (15.0 g, 397 mmol) was slowly added. The mixture was further stirred while being cooled. Additional bismuth trichloride (5.01 g, 15.9 mmol) was then added at an internal temperature of 40° C., followed by addition of sodium borohydride (6.01 g, 159 mmol) and stirring for 55 min at an internal temperature of 40 to 46° C.

While the reaction mixture was cooled and stirred, acetone (41 mL) was added at an internal temperature of 10° C. and the mixture was stirred for 5 min. This was followed by addition of 810 mL of 1 mol/L hydrochloric acid adjusted to pH 1 and ethyl acetate (675 mL) and stirring for 30 min.

The resulting black solid in the reaction mixture was separated by filtration and washed with ethyl acetate (135 mL). The organic layer was separated and collected, and washed sequentially with 0.1 mol/L hydrochloric acid (405 mL), a 5% aqueous sodium bicarbonate solution (405 mL) and 28% brine (405 mL).

The organic layer was concentrated under reduced pressure and was dried at an external temperature of 50° C. for 30 min to give ethyl 3-[4-(3-benzyloxyphenylthio)-2-chlorophenyl]propionate (4) as a pale yellow oil (132 g, equivalent to 318 mmol). Without purification, Compound (4) was dissolved in tetrahydrofuran (THF) (949 mL). While the mixture was being stirred, potassium borohydride (22.3 g, 413 mmol) and then lithium chloride (17.5 g, 413 mmol) were added at an internal temperature of 20° C. and the mixture was stirred for 20 min.

Subsequently, ethanol (47.5 mL) was added and the mixture was stirred for 1 hour at an internal temperature of 30 to 33° C. and then for additional 40 min at an internal temperature of 44 to 45° C. Ethanol (23.7 mL) was then added and the mixture was stirred for additional 30 min at an internal temperature of 43 to 45° C. to complete the reaction. While the reaction mixture was cooled and stirred, acetone (71.2 mL) and then water (475 mL) were added and the mixture was stirred for 1 hour while being cooled. Subsequently, 2 mol/L hydrochloric acid (217 mL, 434 mmol) and then ethyl acetate (475 mL) were added at an internal temperature of 26° C. and the mixture was further stirred.

The organic layer was separated and collected, and washed sequentially with a 5% aqueous sodium bicarbonate solution (475 mL) and 28% brine (475 mL). The organic layer was then concentrated under reduced pressure and was dried at an external temperature of 50° C. under reduced pressure for 1 hour. This gave 3-[4-(3-benzyloxyphenylthio)-2-chlorophenyl]propanol (5) (124 g, equivalent to 318 mmol) as a faint yellow oil.

Without purification, Compound (5) was dissolved in ethyl acetate (1.22 L). Triethylamine (64.3 g, 635 mmol) was added and, while the mixture was being cooled and stirred, methanesulfonyl chloride (54.6 g, 477 mmol) was slowly added dropwise at an internal temperature of 6 to 15° C. The mixture was then stirred for 1 hour at an internal temperature of 5 to 15° C. Subsequently, tap water (1.22 L) was added and the mixture was stirred for 20 min. 6 mol/L hydrochloric acid (26.3 mL, 158 mmol) was then added and the organic layer was separated and collected.

The organic layer was washed sequentially with a 2% aqueous sodium sulfate solution (1.22 L) and a 30% aqueous sodium sulfate solution (612 mL). The organic layer was then concentrated under reduced pressure and the concentrate was dried under reduced pressure at an external temperature of 50° C. for 1 hour. This gave 3-[4-(3-benzyloxyphenylthio)-2-chlorophenyl]propyl methanesulfonate (6) as a pale yellow oil (150 g, equivalent to 318 mmol). Without purification, Compound (6) was dissolved in ethyl acetate (441 mL) and DMF (441 mL). While this mixture was being stirred, sodium iodide (61.9 g, 413 mmol.) was added and the mixture was stirred at an internal temperature of 62 to 65° C. for 3 hours. While the mixture was cooled and stirred, an 8% aqueous sodium sulfate solution (1.32 L) and ethyl acetate (882 mL) were added at an internal temperature of 30° C. The organic layer was separated and collected.

The organic layer was washed by adding sodium thiosulfate pentahydrate (7.35 g) in an 8% aqueous sodium sulfate solution (1.32 L). The organic layer was then washed with a 30% aqueous sodium sulfate solution (662 mL) and the organic layer was separated and collected. The collected organic layer was concentrated under reduced pressure and the concentrate was dried under reduced pressure at an external temperature of 50° C. for 1 hour. This gave 1-benzyloxy-3-[3-chloro-4-(3-iodopropyl)phenylthio]benzene (7) as a yellow oil (160 g, equivalent to 318 mmol). Without purification, Compound (7) was dissolved in DMF (472 mL). While the mixture was being stirred, phloroglucinol dihydrate (12.9 g, 79.4 mmol) and then sodium nitrite (28.5 g, 413 mol) were added and the mixture was stirred at an internal temperature of 29 to 32° C. for 4 hours.

After the mixture was cooled and stirred, sodium thiosulfate pentahydrate 78.9 g (318 mmol) in 5% brine (2.36 L) and ethylacetate (1.57 L) were added for extraction. The organic layer was separated and collected. The organic layer was washed with 5% brine (1.57 L), then twice with a 5% aqueous sodium bicarbonate solution (1.57 L) and then with 28% brine (786 mL). Subsequently, the organic layer was concentrated under reduced pressure and the concentrate was dried at an external temperature of 50° C. for 15 min. The resulting oily residue was dissolved in toluene (157 mL) and the solution was concentrated under reduced pressure.

To the concentrate, additional toluene (157 mL) was added and the solution was concentrated under reduced pressure. The concentrate was dried under reduced pressure at an external temperature of 50° C. for 30 min. This gave a brown oil (134 g). This product was dissolved in toluene (236 mL) and the solution was subjected to silica gel column chromatography (silica gel=393 g) using toluene as an eluant. The desired fractions were combined and concentrated under reduced pressure. The concentrate was dried under reduced pressure at an external temperature of 50° C. for 15 min. The resulting oily residue was dissolved in ethyl acetate (157 mL) and the solution was concentrated under reduced pressure. Additional ethyl acetate (157 mL) was added and the solution was again concentrated under reduced pressure. The concentrate was then dried under reduced pressure at an external temperature of 50° C. for 30 min. This gave 1-benzyloxy-3-[3-chloro-4-(3-nitropropyl)phenylthio]benzene (8) as a pale yellow oil (72.4 g, 175 mmol, 55% yield).

EI-MS m/z: 413 (M$^+$).

$^1$H-NMR (CDCl$_3$, 400 MHz) δ: 2.32 (2H, quint., J=7.1 Hz), 2.81 (2H, t, J=7.3 Hz), 4.40 (2H, t, J=7.1 Hz), 5.03 (2H, s), 6.89-6.98 (3H, m), 7.11-7.41 (9H, m).

Example 3

2-[2-[4-(3-Benzyloxyphenylthio)-2-chlorophenyl]ethyl]-2-nitro-1,3-propanediol (9)

1-Benzyloxy-3-[3-chloro-4-(3-nitropropyl)phenylthio]benzene (8) (72.3 g, 175 mmol) was dissolved in acetonitrile (217 ml). While the solution was cooled and stirred, a 37% formaldehyde solution (14.5 mL, 179 mmol) was added. 1,8-diazabicyclo[5.4.0]undeca-7-ene (DBU) (2.66 g, 17.5 mmol) was then slowly added dropwise at an internal temperature of 0 to 8° C. and the mixture was stirred for 10 min. Subsequently, a 37% formaldehyde solution (14.6 mL, 180 mmol) was added at an internal temperature of 10° C. or below and the mixture was stirred for 1.5 hours at an internal temperature of 2 to 3° C.

To the reaction mixture, 1 mol/L hydrochloric acid (17.5 mL) was added to adjust to pH 3 to 4 and the mixture was stirred for 15 min. The reaction mixture was then concentrated under reduced pressure. The resulting oily residue was dissolved in ethanol (217 mL) and 2 mol/L hydrochloric acid (108 mL) and the solution was stirred at an internal temperature of 45° C. for 30 min. Subsequently, the reaction mixture was concentrated under reduced pressure. To the resulting oily residue, ethyl acetate (723 mL) and 2% brine (361 mL) were added for extraction and the organic layer was separated and collected.

The organic layer was washed sequentially with a 5% aqueous sodium bicarbonate solution (361 mL) and 2% brine (361 mL) and was concentrated under reduced pressure. The concentrate was dried under reduced pressure at an external pressure of 50° C. for 15 min. To the resulting oily residue, methanol (72 mL) was added and the solution was concentrated under reduced pressure. Additional methanol (72 mL) was added and the solution was again concentrated underreducedpressure. The concentrate was then dried under reduced pressure at an external temperature of 50° C. for 30 min to give a pale yellow oil (83.8 g).

This product was dissolved in methanol (723 mL). While the solution was cooled and stirred, tap water (130 mL) was added at an internal temperature of 5 to 10° C. to make the solution cloudy. Crystal seeds were then added to this solution. Once the formation of crystals was confirmed, the mixture was stirred for about 15 min and tap water (593 mL) was added dropwise while the mixture was being stirred. The mixture was cooled while being stirred and was further stirred for 1 hour at an internal temperature of 5 to 10° C. Subsequently, the mixture was left overnight at room temperature. The crystallized solid was collected by filtration and was washed with 50% aqueous methanol (145 mL). The resulting moist crystals were dried by blowing an air stream at room temperature and then blowing an air stream at 30° C. for 16 hours. This gave Compound (9) as a faint yellow powdery crystals (80.7 g, 170 mmol, 98% yield).

mp 69-70° C. (hot plate method).

FAB-MS (positive) m/z: 473[M-H]$^+$.

$^1$H-NMR (CDCl$_3$, 400 MHz) δ: 2.12-2.17 (2H, m), 2.54 (2H, t, J=6.8 Hz), 2.65-2.69 (2H, m), 4.08 (2H, dd, J=6.3, 12.2 Hz), 4.28 (2H, dd, J=7.1, 12.5 Hz), 5.02 (2H, s), 6.88-6.96 (3H, m), 7.08-7.41 (9H, m).

Example 4

2-Amino-2-[2-[4-(3-benzyloxyphenylthio)-2-chlorophenyl]ethyl]-1,3-propanediol hydrochloride (Compound I)

2-[2-[4-(3-Benzyloxyphenylthio)-2-chlorophenyl]ethyl]-2-nitro-1,3-propanediol (9) (80.2 g, 169 mmol) was dissolved in ethanol (802 mL). After the inside atmosphere was replaced with an inert gas atmosphere (argon), 20% palladium hydroxide-carbon (61.5 g (32.1 g dried product)) was added and the atmosphere was replaced with hydrogen. With a hydrogen balloon attached, the reaction mixture was vigorously stirred for 24 hours at an external temperature of 50° C.

The atmosphere was replaced with inert gas (argon) and the catalyst was separated by filtration at an internal temperature of 30° C. The remaining mixture was washed with 90% aqueous ethanol (401 mL). The filtrate was concentrated under reduced pressure and the concentrate was then dried under reduced pressure at an external temperature of 50° C. for 15 min. To this product, acetonitrile (80 mL) was added and the mixture was concentrated under reduced pressure. Additional acetonitrile (80 mL) was added and the mixture was again concentrated under reduced pressure. The concentrate was then dried under reduced pressure at an external temperature of 50° C. for 30 min.

To the resulting residue, acetonitrile (401 mL) was added and the mixture was stirred at an internal temperature of 65 to 70° C. for 30 min. The mixture was then allowed to cool while being stirred and then cooled while being stirred. Subsequently, the mixture was stirred at an internal temperature of 5 to 10° C. for 30 min. The crystallized solid was collected by filtration, washed with acetonitrile (160 mL, internal temperature=1° C.), and dried at room temperature to obtain crude crystals (44.9 g). To this product, acetonitrile (201 mL) was added and the mixture was stirred at an internal temperature of 65 to 70° C. for 30 min. Subsequently, the mixture was allowed to cool while being stirred and was then stirred at an internal temperature of 3 to 10° C. for 1 hour. The crystallized solid was collected by filtration and washed with acetonitrile (120 mL) (internal temperature=2° C.).

The washed product was dried under an air stream and further dried by blowing an air stream at 50° C. for 3 hours. This resulted in a white powder (42.4 g) To this product, acetonitrile (170 mL) and purified water (170 mL) were added and the mixture was stirred and heated to dissolve the solid product. The solution was cooled while being stirred. This resulted in the formation of crystals at an internal temperature of 40° C. The mixture was further cooled while being stirred. The mixture was further stirred at an internal temperature of 3 to 10° C. for 1 hour. The crystallized solid was collected by filtration and washed with 50% aqueous acetonitrile (127 mL, internal temperature=2° C.). The washed product was dried under an air stream for 1 hour. This product was further dried for 14 hours by blowing an air stream at 50° C. to give white powdery crystals (38.4 g). To this product (38.2 g), ethanol (229 mL) was added and the mixture was stirred and heated to dissolve the solid product. The solution was filtrated and washed with ethanol (38 mL).

The filtrate was stirred while being heated and 6 mol/L hydrochloric acid (15.8 mL, 94.8 mmol) was added at an internal temperature of 60° C. (Crystallization was confirmed). This was followed by addition of ethyl acetate (535 mL) and stirring for 10 min at an internal temperature of 50 to 58° C. Subsequently, the mixture was cooled while being stirred, and was further stirred for 1 hour at an internal temperature of 1 to 10° C. The crystallized solid was collected by filtration and was washed with a mixture of ethanol (57 mL) and ethyl acetate (57 mL). The washed product was dried under an air stream for 1 hour to obtain moist crystals, which were further dried for 15 hours by blowing an air stream at 60° C. The dried product was crushed to obtain Compound I as white powdery crystals (38.3 g, 79.7 mmol, 47% yield).

mp 158-160° C. (hot plate method).

FAB-MS (positive) m/z: 444[$C_{24}H_{26}ClNO_3S$+H]$^+$.

Elemental analysis: Calcd for $C_{24}H_{26}ClNO_3S\cdot HCl$: C, 60.00, H, 5.66, N, 2.92; found: C, 59.83; H, 5.51; N, 2.85.

$^1$H-NMR (DMSO-d$_6$, 400 MHz) δ: 1.75-1.79 (2H, m), 2.71-2.75 (2H, m), 3.54 (4H, d, J=5.1 Hz), 5.08 (2H, s), 5.42 (2H, t, J=4.9 Hz), 6.88-7.00 (3H, m), 7.23-7.41 (9H, m), 7.93 (3H, br s).

INDUSTRIAL APPLICABILITY

The use of any of the novel compounds of the present invention (i.e., ethyl 3-[4-(3-benzyloxyphenylthio)-2-chlorophenyl]acrylate, 1-benzyloxy-3-[3-chloro-4-(3-nitropropyl)phenylthio]benzene and 2-[2-[4-(3-benzyloxyphenylthio)-2-chlorophenyl]ethyl]-2-nitro-1,3-propanediol) as an intermediate in the production of Compound I, an effective immunosuppressant, enables simple and industrially practical production of Compound I at high purity and stable yield. It has thus been demonstrated that the present invention offers a way to provide high quality Compound I in high yield.

The present invention establishes an industrially advantageous process for producing Compound I, an effective immunosuppressant. Compound I produced by the process of the present invention can be used to as high purity and high quality pharmaceutical products.

The invention claimed is:

1. A process for producing 2-amino-2[2-[4-(3-benzyloxyphenylthio)-2-chlorophenyl]ethyl]-1,3-propanediol hydrochloride, comprising the steps of:
    reacting 4-(3-benzyloxyphenylthio)-2-chlorobenzaldehyde with ethyl diethylphosphonoacetate in a solvent in the presence of a base to form ethyl 3-[4-(3-benzyloxyphenylthio)-2-chlorophenyl]acrylate;
    reducing the resulting ethyl 3-[4-(3-benzyloxyphenylthio)-2-chlorophenyl]acrylate, followed by mesylation, iodination and nitration, to form 1-benzyloxy-3-[3-chloro-4-(3-nitropropyl)phenylthio]benzene;
    hydroxymethylating the resulting 1-benzyloxy-3-[3-chloro-4-(3-nitropropyl)phenylthio]benzene with formaldehyde to form 2-[2-[4-(3-benzyloxyphenylthio)-2-chlorophenyl]ethyl]-2-nitro-1,3-propanediol; and
    reducing the resulting 2-[2-[4-(3-benzyloxyphenylthio)-2-chlorophenyl]ethyl]-2-nitro-1,3-propanediol in the presence of a palladium catalyst to form the desired product.

2. A process for producing 2-amino-2-[2-[4-(3-benzyloxyphenylthio)-2-chlorophenyl]ethyl]-1,3-propanediol hydrochloride, comprising the step of reducing 2-[2-[4-4(3-benzyloxyphenylthio)-2-chlorophenyl]ethyl]-2-nitro-1,3-propanediol in the presence of a palladium catalyst.

3. The production process according to claim 2, wherein the reduction step is performed using a palladium hydroxide-carbon catalyst.

4. The production process according to claim 1, wherein the reduction step is performed using a palladium hydroxide-carbon catalyst.

* * * * *